US011234592B2

(12) United States Patent
Berner et al.

(10) Patent No.: US 11,234,592 B2
(45) Date of Patent: Feb. 1, 2022

(54) ARRANGEMENT FOR ADAPTING THE FOCAL PLANE OF AN OPTICAL SYSTEM TO A NONPLANAR, IN PARTICULAR SPHERICAL OBJECT

(71) Applicant: Carl Zeiss Meditec AG, Jena (DE)

(72) Inventors: Andrea Berner, Jena (DE); Ingo Koschmieder, Jena (DE); Dietrich Martin, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 256 days.

(21) Appl. No.: 16/472,051

(22) PCT Filed: Dec. 15, 2017

(86) PCT No.: PCT/EP2017/082953
§ 371 (c)(1),
(2) Date: Jun. 20, 2019

(87) PCT Pub. No.: WO2018/114636
PCT Pub. Date: Jun. 28, 2018

(65) Prior Publication Data
US 2019/0374101 A1    Dec. 12, 2019

(30) Foreign Application Priority Data
Dec. 22, 2016  (DE) ............... 10 2016 226 002.2

(51) Int. Cl.
*A61B 3/135*  (2006.01)
*A61B 3/12*  (2006.01)
(Continued)

(52) U.S. Cl.
CPC ............ *A61B 3/135* (2013.01); *A61B 3/12* (2013.01); *A61B 3/14* (2013.01); *G02B 27/0068* (2013.01)

(58) Field of Classification Search
CPC .. A61B 3/135; A61B 3/12; A61B 3/14; G02B 27/0068
(Continued)

(56) References Cited

U.S. PATENT DOCUMENTS

| 4,248,506 A | 2/1981 | Takahashi |
| 5,139,022 A | 8/1992 | Lempert |

(Continued)

FOREIGN PATENT DOCUMENTS

| DE | 103 07 741 A1 | 9/2004 |
| DE | 10 2004 028 471 A1 | 12/2005 |

(Continued)

OTHER PUBLICATIONS

English translation of PCT International Preliminary Report on Patentability for International Application No. PCT/EP2017/0825953, dated Dec. 15, 2017, 8 pages.

(Continued)

*Primary Examiner* — Mohammed A Hasan
(74) *Attorney, Agent, or Firm* — Patterson Thuente Pedersen, P.A.

(57) ABSTRACT

An arrangement for adapting the focal plane of an optical system to a non-planar, in particular spherical or spheroidal object, wherein the optical system has a positive total refractive power and generates a real image. The optical system also comprises an optical element with a negative refractive power. Principally useful in all technical fields with the corresponding requirements relating to a curved focal plane, the arrangement is useful in ophthalmologic devices. The eye which is to be examined is the spherical or spheroidal object for example, the front of the eye which has radii of between 5 and 10 mm of small dimensions.

27 Claims, 3 Drawing Sheets

(51) Int. Cl.
*A61B 3/14* (2006.01)
*G02B 27/00* (2006.01)

(58) Field of Classification Search
USPC .......................................................... 351/214
See application file for complete search history.

(56) References Cited

U.S. PATENT DOCUMENTS

| | | | |
|---|---|---|---|
| 5,404,884 A | 4/1995 | Lempert | |
| 6,275,718 B1 | 8/2001 | Lempert | |
| 2003/0218755 A1* | 11/2003 | Wei | A61B 3/102 356/497 |
| 2014/0132922 A1 | 5/2014 | Padrick | |
| 2015/0205083 A1 | 7/2015 | Dolgin | |
| 2017/0363851 A1* | 12/2017 | Xu | G02B 21/361 |

FOREIGN PATENT DOCUMENTS

| | | | |
|---|---|---|---|
| FR | 1 156 545 A | | 5/1958 |
| JP | 2000 135200 A | | 5/2000 |
| JP | 2000135200 A | * | 5/2000 |

OTHER PUBLICATIONS

International Search Report and Written Opinion for International Application No. PCT/EP2017/082953, dated May 7, 2018, 38 pages.
English translation of International Search Report for International Application No. PCT/EP2017/082953, dated May 7, 2018, 3 pages.
German Search Report for Application No. 10 2016 226002.2, dated Jul. 14, 2017, 9 pages.

* cited by examiner

ARRANGEMENT FOR ADAPTING THE FOCAL PLANE OF AN OPTICAL SYSTEM TO A NONPLANAR, IN PARTICULAR SPHERICAL OBJECT

RELATED APPLICATIONS

This application is a National Phase entry of PCT Application No. PCT/EP2017/082953 filed Dec. 15, 2017, which application claims the benefit of priority to DE Application No. 10 2016 226 002.2, filed Dec. 22, 2016, the entire disclosures of which are incorporated herein by reference.

TECHNICAL FIELD

The present invention relates to a solution to the problem addressed by the invention, with which the focal plane (or image field) of an optical system can be adapted to a non-planar, in particular spherical, object. As a result, it is possible to illuminate or image non-planar objects in a lighting or imaging system in a targeted manner, such that they are in focus all the way to the edge.

BACKGROUND

In simple optical systems that generate a real image and thus have a positive total refractive power, the image field is fundamentally curved in a concave manner toward the object. The image curvature of the system is therefore negative.

In this regard, FIG. 1 shows, by way of example, the course of an image field curvature of a simple optical system. The image field curvature of the sagittal and tangential image surfaces on a planar reference image plane is shown therein. A curved ideal focal plane $FC_{ideal}$ is obtained, which lies between the sagittal focal plane $FC_{sag}$ and the tangential focal plane $FC_{tan}$. The ideal focal plane $FC_{ideal}$ is curved in a concave manner toward the object.

According to the known prior art, lighting and imaging systems are known that are optimized such that a planar focal plane is obtained or used.

If objects that are not planar, but instead spherical, are illuminated or imaged with such a system, this necessarily leads to a qualitative reduction in the capacity of the optical imaging, because the object does not fulfill the implicit assumption of the design. As a result, projected structures only exhibit the necessary image sharpness in the middle of the image field, e.g. at the apex of the spherical curvature. In the outer edge regions, small structures in particular are out of focus, and there is a significant loss in intensity. This makes it more difficult to evaluate these structures, and they can only be evaluated to a limited extent. If instead, the edge region is in focus, although the structures there are in focus, the center of the image will necessarily be out of focus.

This is particularly disadvantageous when measurements are based on the evaluation or depiction of structures over the entire range of the image field of the non-planar surface.

If the spherical objects tend to have smaller radii, it must be assumed that the optical systems used so far only allow for a good optical imaging with a limited depth of field.

The lighting systems used in ophthalmological devices normally generate focal planes that are curved in the opposite direction of the surface of the cornea of the eye. As a result, structures, and in particular small structures, e.g. lines, can only be in focus and detected in a small area, i.e. either only at the edge or only at the apex.

A uniform focusing on an optical slit on the cornea of the eye over its entire length with such an optical system is not possible without taking special measures.

With the ophthalmological devices currently in use, an image plane that is flat or curved in the opposite direction is disadvantageous for the lighting or irradiating components. As a result, only the structures projected into or onto the eye at the middle of the image field, at the visual axis, exhibit the necessary image sharpness. The fine structures in the outer and edge regions are fanned out, become unfocused, and have a significantly lower intensity. It is thus difficult to evaluate these structures, and this is only possible within a limited range.

With a slit lamp this is clear in that the slit projected onto the eye is not in focus over the entire length, and thus the edge sharpness necessary for measurement purposes cannot be obtained over the entire length of the slit.

Methods and assemblies for lighting the front portion of the eye are described in U.S. Pat. Nos. 5,404,884; 5,139,022 and 6,275,718, in which a planar configured laser is used as the light source. The physically limited depth of field of the imaging system for the diffused light reflected by the eye is disadvantageous with these systems, such that the expansion range of the focused laser cross section cannot be fully recorded.

Systems according to the known prior art with which image fields are shaped in a targeted manner in order to adjust them to different curvatures of the object are known.

By way of example, an assembly is described in DE 103 07 741 A1, for example, with which the image field of the lighting or irradiating components of ophthalmological diagnosis and therapy devices is improved. The assembly is suitable in particular for ophthalmological devices in which a uniformly high imaging quality over large areas of the eye is of interest. A diffractive optical element (DOE) is located in the light beam path of the irradiating unit for this, in order to shape the image plane in a target manner. The diffractive optical element can be located on the surface of another optical element, or it can be a separate element.

Although the type of light source that is used as well as the type of beam formation, i.e. the structure or pattern generation, is irrelevant, the diffractive effect, however, depends on the wavelength. This is disadvantageous in particular with the various lighting and observation modes of ophthalmological devices. Moreover, the diffractive structures are difficult and complicated to produce.

SUMMARY OF THE INVENTION

Embodiments of the present invention seek to eliminate the mitigate disadvantages known from the prior art, and to propose a solution with which the focal plane of an optical system can be adapted to a non-planar, in particular spherical or spheroidal, object, such that projected structures, images, drawings, etc. exhibit a uniformly high imaging quality over wide ranges of the object. Furthermore, embodiments of the invention are equally suitable for both lighting as well as imaging systems.

According to embodiments of the invention, the assembly for adapting a focal plane of an optical system to a non-planar, in particular spherical or spheroidal, object the optical system has a positive total refractive power and generates a real image, and there is at least one additional optical element with a negative refractive power therein.

Although the proposed solution for adapting the focal plane of an optical system to a non-planar, in particular spherical or spheroidal, object of different dimensions can primarily be used in any technological field that requires a curved focal plane, its use in ophthalmological devices is of particular interest. The eye that is to be examined, and in particular the front surface of the eye, forms the spherical or spheroidal object, which tends to have smaller dimensions, with radii of 5 to 10 mm.

BRIEF DESCRIPTION OF THE DRAWINGS

The invention shall be explained below in greater detail based on exemplary embodiments. In this regard.

DETAILED DESCRIPTION

Figure 1:
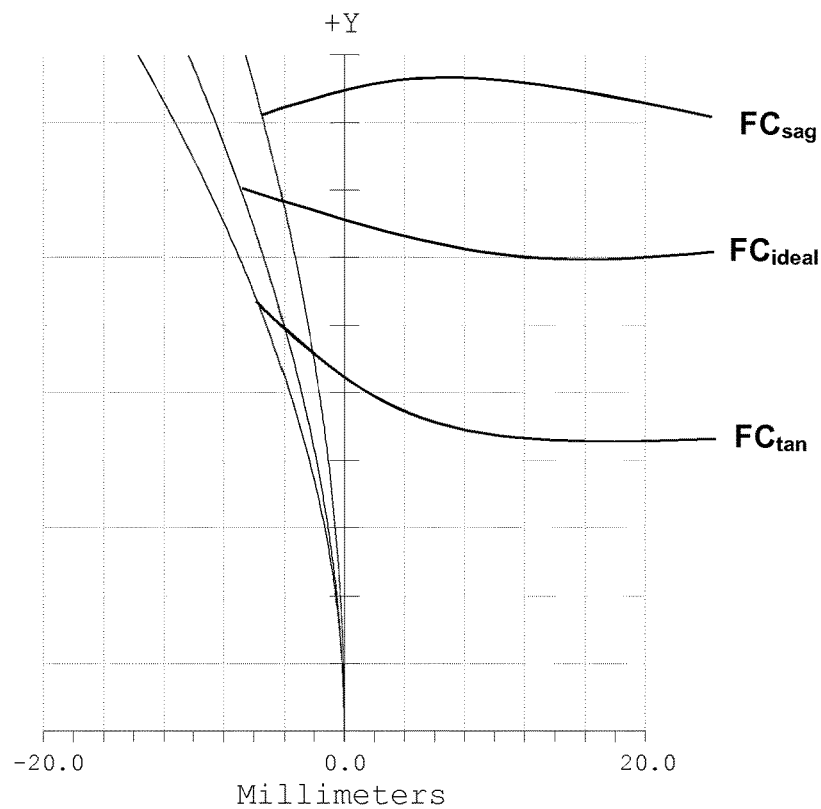
FIG. 1 depicts the course of the image field curvature in a simple optical system.

In the assembly for adapting the focal plane of an optical system to a non-planar, in particular spherical or spheroidal, object, the optical system has a positive total refractive power, and generates a real image. According to embodiments of the invention, the optical system has at least one additional optical element with a negative refractive power.

It is of particular advantage that the optical system can be used in a lighting assembly as well as an imaging assembly. For this, the focal plane of an optical system is optimized such that it is adapted to the curved surface of the object that is to be illuminated, or imaged as precisely as possible.

Appropriate lenses and/or mirrors that have a negative refractive power are used as the additional optical element.

According to embodiments of the invention, the dimensions of the negative refractive power of the additional optical element that is used are such that the sum of the sagittal and tangential image field curvature portions of the total optical system is positive. In dimensioning the negative refractive power of the additional optical element, its material coefficients are taken into account in particular.

The relationships for lighting curved objects shall be explained below. It should be noted, however, that the same conditions also apply to imaging curved objects onto a planar surface, e.g. an imaging sensor.

A convex curved object is to be illuminated with the lighting system (from the perspective of the light source). For this, the focal plane of the lighting system is intentionally also curved in a convex manner.

This is possible through the targeted addition of negative refractive powers, corresponding to the lens contributions for the sagittal and tangential image field curvatures $FC_{sag}$ and $FC_{tan}$. The material coefficients and selection of the appropriate type of glass must also be taken into account thereby.

The lens contributions for the sagittal and tangential image field curvature are calculated as follows:

$$FC_{sag} = S_3 + S_4 \quad (1)$$

$$FC_{tan} = 3S_3 + S_4 \quad (2)$$

when $$S_3 = H^2 F$$

$$S_4 = H^2 F/n$$

where $S_3$ is the apex coefficient for astigmatism,
$S_4$ is the apex coefficient for the Petzval image field curvature, H is the Lagrange invariant of the system (H=nuy=n'u'y'),
n is the refractive index of the lens, and
F is the refractive power of the lens.

For an ideal image plane with a convex curvature, FCsag and FCtan must be negative. By adding negative refractive powers in a targeted manner, in addition to the positive portions of the existing convex lenses, portions of negative effects regarding the image field curvature are also added together. With the targeted use of an optical element that has a negative refractive power, the sums of the sagittal and tangential image curvature portions of the total optical system become negative, thus resulting in an ideal imaging plane with a convex curvature between the sagittal and tangential image field curvature surface. The focal plane of a lighting or imaging system is thus optimized, such that it is adapted as precisely as possible to the curved outer contour of the object that is to be illuminated or imaged.

Figure 2:
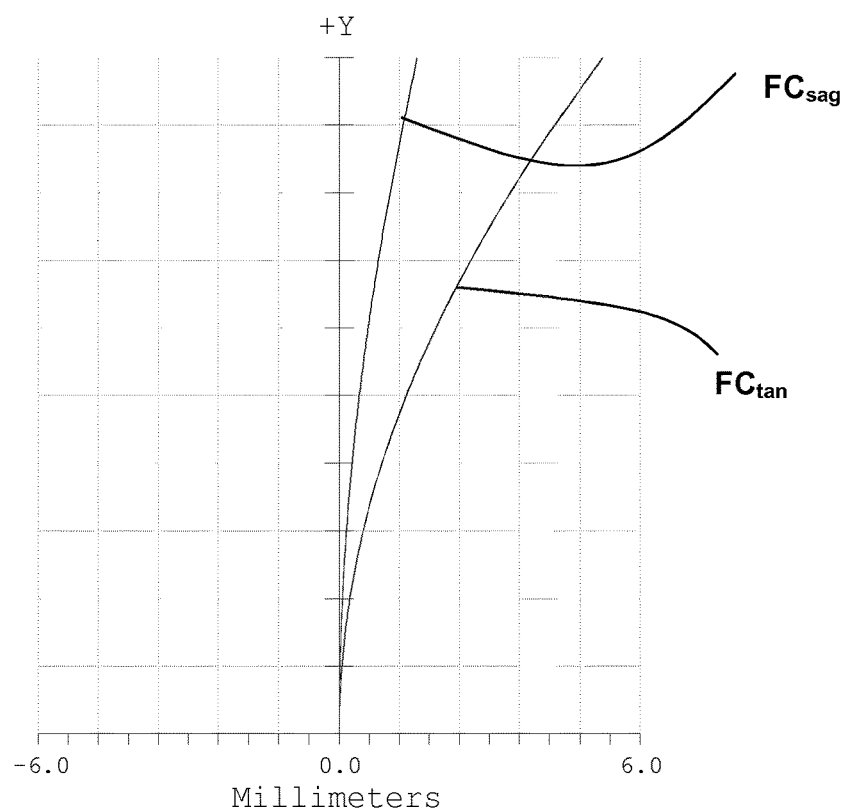
FIG. 2 depicts the course of the image field curvature in an optical system according to the invention.

In this regard, FIG. 2 shows, by way of example, the course of the image field curvature of an optical system according to an example embodiment of the invention. The image field curvatures of the sagittal and tangential image surfaces on a planar reference imaging plane are also shown therein. A curved ideal focal plane $FC_{ideal}$ (not shown) is also obtained therein, which likewise lies between the sagittal focal plane $FC_{sag}$ and the tangential focal plane $FC_{tan}$. In differing from the image field curvature of a simple optical system shown in FIG. 1, the ideal focal plane $FC_{ideal}$, however, is negative, i.e. it is curved in a convex manner corresponding to the curvature of the object.

Figure 3:
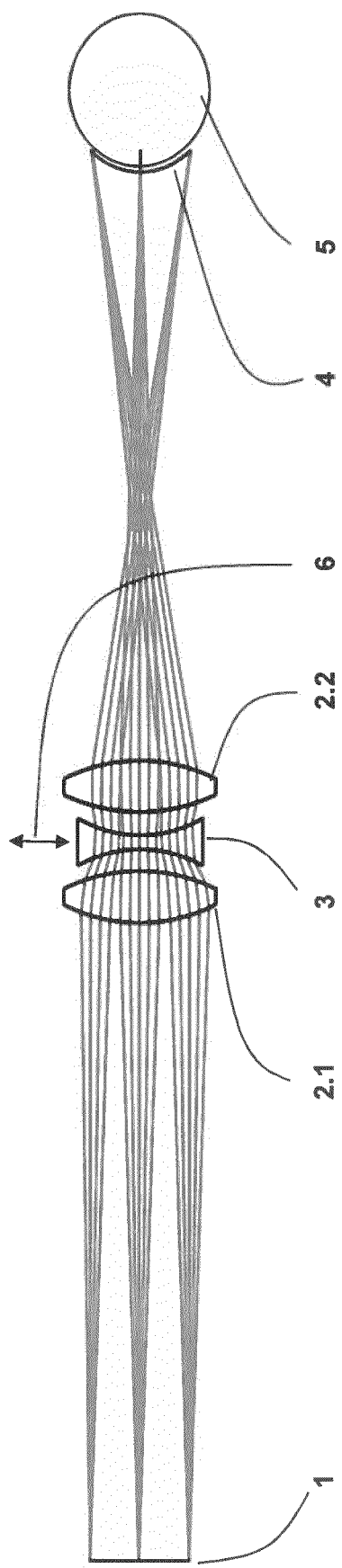
FIG. 3 depicts the schematic structure of a lighting system according to the invention.

The corresponding schematic structure of a lighting system according to the invention is shown in FIG. 3, which includes a light source 1 and a lens system composed of two convex lenses 2.1 and 2.2. A lens 3 is used therein for the additional optical element with negative refractive power, which is dedicated to the two convex lenses 2.1 and 2.2. The lens 3 used for curving the focal plane 4 of the overall optical system is for example located between the two convex lenses 2.1 and 2.2. The object with the spherical curvature that is to be illuminated is indicated by the numeral 5. The double arrow 6 indicates how the lenses with negative refractive power can be exchanged in order to adapt the system to spherical objects with different radii. The planar surface of the light source 1 is thus mapped in an ideal manner onto the object 5 that has a convex curvature, because the resulting focal plane 4 likewise has a convex curvature. It should also be noted that the schematic structure of a lighting system shown in FIG. 3 also applies analogously, in accordance with the invention, to an imaging system, under the same conditions. The light reflected by a curved object is imaged on a (planar) image sensor, which would be located at the position of the light source, by the two convex lenses and the additional lens with negative refractive power located therebetween.

The use of the optical system according to the invention is particularly advantageous for both lighting as well as imaging. As a result, it is possible to illuminate a curved object with a planar light source (with an adapted curved focal plane), and to image the light reflected by a curved object (with an adapted planar focal plane) on a planar image sensor.

In an example embodiment, there are numerous additional optical elements in the form of lenses with negative refractive power, which can be exchanged in order to adapt the system to spherical objects of different radii.

In another example embodiment, a lens is used for adapting the optical system to spherical or spheroidal objects with different radii, the optical properties of which can be varied.

This offers the possibility of not only adapting the optical system to spherical or spheroidal objects with different radii, but also to planar objects. Electric optical systems or even variable lenses, e.g. liquid or rubber lenses, or gel-based lenses are also conceivable for this.

The lenses or their optical properties can be selected manually in a targeted manner for this. It is also possible to use a camera and a corresponding image evaluation in order to automate the selection.

The additional optical element in the form of a lens offers the advantage, for example, that it can be used to correct the optical system with regard to color aberrations, distortions, etc.

According to another example embodiment, the use of the optical system according to the invention in an ophthalmological device is particularly advantageous. The non-planar, in particular spherical, object corresponds to the eye. The optical system can also be used as both a lighting system and an imaging system in an ophthalmological device.

If the optical system is to be used in a slit lamp in order to light the cornea, there are other additional boundary conditions, such as ensuring a sufficient working distance and a predefined position of the pupil. Taking these boundary conditions into account requires that the optical system be adapted appropriately.

In order to use the optical system in a slit lamp, it must be ensured that there is a sufficient working distance to the eye for additional imaging optics. The additional imaging optics is for example designed such that it can be displaced for the movement of the slit imaging along the optical axis.

Figure 4:
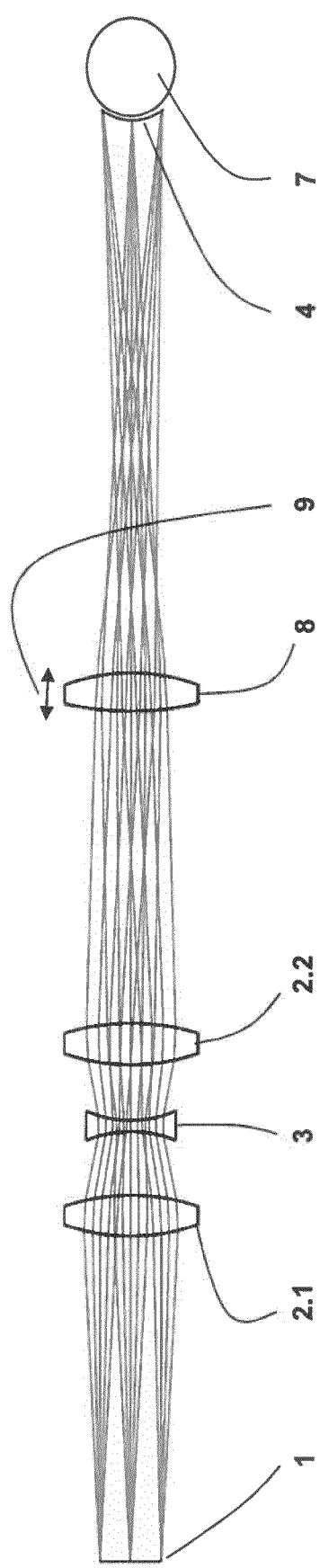
FIG. 4 depicts the schematic structure of a lighting system according to the invention for a slit lamp.

The corresponding schematic structure of a lighting system according to the invention for a slit lamp is shown in FIG. 4, which comprises a light source 1 and a lens system composed of two convex lenses 2.1 and 2.2. A lens 3 is used therein as an additional optical element with negative refractive power, which is dedicated to the two convex lenses 2.1 and 2.2. The lens 3 used for the curvature of the focal plane 4 of the overall optical system is for example located between the two convex lenses 2.1 and 2.2. FIG. 4 also shows the eye 6 that is to be illuminated, and the additional imaging optics 8 for ensuring a sufficient working distance. The double arrow 9 indicates that the imaging optics 8 is designed such that it can be displaced along the optical axis for the movement of the slit imaging.

In an advantageous example embodiment of the lighting system according to the invention for a slit lamp according to FIG. 4, the individual lenses, or the lens system, have focal lengths in the following ranges:

lens 3: f'=−5 to −30 mm
lens system (2.1, 2.2, and 3): f'=50 to 150 mm
imaging optics 8: f'=25 to 125 mm According to a particularly preferred example embodiment, the individual lenses, or the lens system, have focal lengths in the following ranges:

lens 3: f'=−10 to −20 mm
lens system (2.1, 2.2, and 3) f'=80 to 120 mm
imaging optics 8: f'=50 to 100 mm The planar surface of the light source 1 is thus mapped here as well onto the convex curvature of the eye 7 in an ideal manner, because the resulting focal plane 4 is likewise curved in a convex manner. It should also be noted that the schematic structure of a lighting system for a slit lamp shown in FIG. 4 can likewise be used analogously for an imaging system under the same conditions.

The use of the optical system according to example embodiments of the invention is particularly advantageous for both lighting as well as imaging. As a result, it is possible to light an eye with a planar lighting source (with a curved focal plane adapted thereto), and to image the light (with a planar focal plane adapted thereto) reflected by the eye on a planar image sensor.

According to an example embodiment, the additional optical element in the form of a lens with negative refractive power is designed such that slit images of up to 16 mm can be imaged.

According to another example embodiment, it is advantageous to design the additional optical element in the form of a lens with negative refractive power such that curvature radii R of the cornea of the eye between 5 mm and 10 mm can be covered with an image field diameter (or lighting field diameter) of 5-20 mm.

According to a further example embodiment, it is advantageous when the additional optical element with negative refractive power is designed such that the ideal focal plane $FC_{ideal}$ is in the middle, between the sagittal focal plane $FC_{sag}$ and the tangential focal plane $FC_{tan}$, and exhibits minimal deviations from the non-planar, in particular spherical, object. It is particularly advantageous, for example, when the minimal deviations lie within the depth of field of the system.

Figure 5:
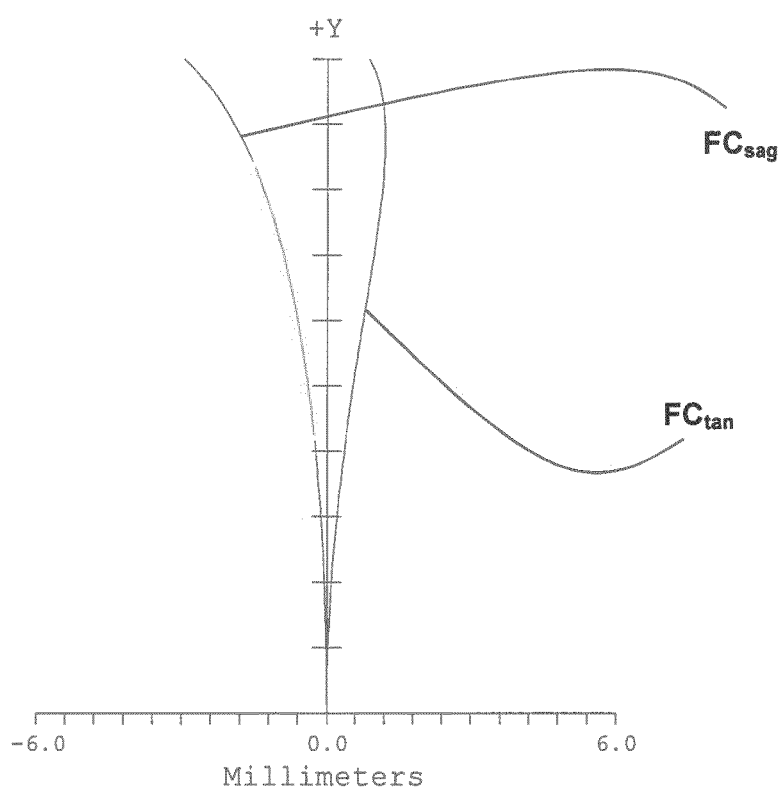
FIG. 5 depicts the course of the image curvature of the optical system according to the invention for a slit lamp.

Lastly, FIG. 5 shows the course of the image field curvature of the optical system according to the invention for a slit lamp.

The course of the image field curvature for the system according to FIG. 4 is shown herein, measured, however, in differing from the illustrations in FIGS. 1 and 2, on a curved imaging plane with a radius of 8 mm.

It can be seen therein that the ideal imaging plane, which likewise lies between the sagittal focal plane $FC_{sag}$ and the tangential focal plane $FC_{tan}$, has a minimal deviation of 0, corresponding to a minimal deviation of the non-planar, in particular spherical, object.

This shows that the optical system is adapted in an ideal manner to a spherical object with a radius of 8 mm for lighting purposes.

An assembly for adapting the focal plane of an optical system to a non-planar, in particular spherical, object is obtained with the solution to the problem addressed by the invention, with which the focal plane of an optical system can be adapted to a non-planar, in particular spherical or spheroidal, object. As a result, it is possible to illuminate or image non-planar objects in a targeted manner, such that they are in focus all the way to the edge, in optical lighting or imaging systems. This solution is equally suitable for both lighting systems and imaging systems.

The proposed solution can be used in theory in any technological field that has the corresponding demands of a curved focal plane, but is particularly suitable for use in ophthalmological devices with object radii of 5 to 10 mm.

The proposed solution can be optimized not only for monochromatic light sources, but also for light sources with a wide spectrum (white light).

The invention claimed is:

1. An assembly for adapting the focal plane of an optical system to a non-planar object,
   wherein the optical system exhibits a positive total refractive power, and generates a real image,
   comprising at least one additional optical element with negative refractive power, usable in both a lighting assembly and an imaging assembly;
   wherein the at least one additional optical element is a lens, a mirror or a combination of both thereof, the negative refractive power of the additional optical element being dimensioned such that the sums of sagittal and tangential image field curvature portions of the overall optical system are negative;

wherein the at least one additional optical element corrects the optical system with regard to at least color aberrations and distortion;

wherein the optical system is usable in an ophthalmological device as both a lighting system and an imaging system; and wherein the at least one additional optical element with negative refractive power is designed such that slit images of up to 20 mm can be recorded.

2. The assembly according to claim 1, wherein the non-planar object is spherical or spheroidal.

3. The assembly according to claim 1, wherein material coefficients of the at least one additional optical element are taken into account in the dimensioning of the negative refractive power.

4. The assembly according to claim 1, further comprising numerous additional optical elements with negative refractive power, which are exchangeable to adapt the system to spherical objects with different radii.

5. The assembly according to claim 1, further comprising further optical elements that adapt the optical system to spherical objects with different radii, the optical properties of the further optical elements being variable.

6. The assembly according to claim 1, wherein the optical system is used in an ophthalmological device, wherein the non-planar object corresponds to an eye.

7. The assembly according to claim 6, wherein the optical system is used in a slit lamp, and further comprising additional imaging optics to establish a sufficient working distance to the eye.

8. The assembly according to claim 7, wherein the additional imaging optics are designed such that they are displaceable along an optical axis for the movement of slit imaging.

9. The assembly according to claim 1, wherein the minimal deviations lie within the depth of field of the system.

10. An assembly for adapting the focal plane of an optical system to a non-planar object, wherein the optical system exhibits a positive total refractive power, and generates a real image, comprising at least one additional optical element with negative refractive power, usable in both a lighting assembly and an imaging assembly;

wherein the at least one additional optical element is a lens, a mirror or a combination of both thereof, the negative refractive power of the additional optical element being dimensioned such that the sums of sagittal and tangential image field curvature portions of the overall optical system are negative;

wherein the at least one additional optical element corrects the optical system with regard to at least color aberrations and distortion;

wherein the optical system is usable in an ophthalmological device as both a lighting system and an imaging system; and wherein the at least one additional optical element with negative refractive power is designed such that curvature radii R of the cornea of the eye between 5 mm and 10 mm are covered with an image field diameter of 5-20 mm.

11. The assembly according to claim 10, wherein the non-planar object is spherical or spheroidal.

12. The assembly according to claim 10, wherein material coefficients of the at least one additional optical element are taken into account in the dimensioning of the negative refractive power.

13. The assembly according to claim 10, further comprising numerous additional optical elements with negative refractive power, which are exchangeable to adapt the system to spherical objects with different radii.

14. The assembly according to claim 10, further comprising further optical elements that adapt the optical system to spherical objects with different radii, the optical properties of the further optical elements being variable.

15. The assembly according to claim 10, wherein the optical system is used in an ophthalmological device, wherein the non-planar object corresponds to an eye.

16. The assembly according to claim 15, wherein the optical system is used in a slit lamp, and further comprising additional imaging optics to establish a sufficient working distance to the eye.

17. The assembly according to claim 16, wherein the additional imaging optics are designed such that they are displaceable along an optical axis for the movement of slit imaging.

18. The assembly according to claim 10, wherein the minimal deviations lie within the depth of field of the system.

19. An assembly for adapting the focal plane of an optical system to a non-planar object, wherein the optical system exhibits a positive total refractive power, and generates a real image, comprising at least one additional optical element with negative refractive power, usable in both a lighting assembly and an imaging assembly;

wherein the at least one additional optical element is a lens, a mirror or a combination of both thereof, the negative refractive power of the additional optical element being dimensioned such that the sums of sagittal and tangential image field curvature portions of the overall optical system are negative;

wherein the at least one additional optical element corrects the optical system with regard to at least color aberrations and distortion;

wherein the optical system is usable in an ophthalmological device as both a lighting system and an imaging system; and wherein the at least one additional optical element with negative refractive power is designed such that the ideal focal plane $FC_{ideal}$ of the overall system, which lies in between the sagittal focal plane $FC_{sag}$ and the tangential focal plane $FC_{ideal}$, exhibits a minimal deviation to the non-planar object.

20. The assembly according to claim 19, wherein the non-planar object is spherical or spheroidal.

21. The assembly according to claim 19, wherein material coefficients of the at least one additional optical element are taken into account in the dimensioning of the negative refractive power.

22. The assembly according to claim 19, further comprising numerous additional optical elements with negative refractive power, which are exchangeable to adapt the system to spherical objects with different radii.

23. The assembly according to claim 19, further comprising further optical elements that adapt the optical system to spherical objects with different radii, the optical properties of the further optical elements being variable.

24. The assembly according to claim 19, wherein the optical system is used in an ophthalmological device, wherein the non-planar object corresponds to an eye.

25. The assembly according to claim 24, wherein the optical system is used in a slit lamp, and further comprising additional imaging optics to establish a sufficient working distance to the eye.

26. The assembly according to claim 25, wherein the additional imaging optics are designed such that they are displaceable along an optical axis for the movement of slit imaging.

27. The assembly according to claim 19, wherein the minimal deviations lie within the depth of field of the system.

* * * * *